United States Patent
Higashi et al.

(10) Patent No.: US 10,378,416 B2
(45) Date of Patent: Aug. 13, 2019

(54) ANALYZING APPARATUS AND EXHAUST GAS TREATING SYSTEM

(71) Applicant: FUJI ELECTRIC CO., LTD., Kanagawa (JP)

(72) Inventors: Ryoichi Higashi, Hino (JP); Masaya Tabaru, Hino (JP); Kazuhiro Koizumi, Sagamihara (JP); Michiyasu Okada, Hachioji (JP); Kozo Akao, Tama (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 271 days.

(21) Appl. No.: 15/164,894

(22) Filed: May 26, 2016

(65) Prior Publication Data
US 2016/0348561 A1 Dec. 1, 2016

(30) Foreign Application Priority Data
May 29, 2015 (JP) .................. 2015-109703

(51) Int. Cl.
*G01N 1/22* (2006.01)
*F01N 11/00* (2006.01)
(Continued)

(52) U.S. Cl.
CPC ............ *F01N 11/007* (2013.01); *F01N 3/021* (2013.01); *F01N 3/04* (2013.01); *G01M 15/102* (2013.01);
(Continued)

(58) Field of Classification Search
CPC ... G01N 2021/0193; G01N 2021/0389; G01N 2021/151; G01N 2021/158;
(Continued)

(56) References Cited

U.S. PATENT DOCUMENTS 2,895,335 A * 7/1959 Kraftson .............. G01N 1/4077
73/863.12
2,930,237 A 3/1960 Fowle, Jr. et al.
(Continued)

FOREIGN PATENT DOCUMENTS

DE 10318786 A1 11/2004
JP S52-033792 A 3/1977
(Continued)

OTHER PUBLICATIONS

European search report issued for counterpart European Application 16171379.7, issued by European Patent Office dated Nov. 4, 2016.
(Continued)

*Primary Examiner* — Son T Le
*Assistant Examiner* — Alexander A Mercado

(57) ABSTRACT

It is aimed to analyze a gas component of a to-be-analyzed gas with a reduced influence of a liquid component contained in the to-be-analyzed gas. Provided is an analyzing apparatus for analyzing a gas component of an exhaust gas that has passed through a scrubber apparatus and the like. The analyzing apparatus includes a collecting nozzle configured to collect a to-be-analyzed gas, a liquid collecting unit configured to collect a liquid component contained in the to-be-analyzed gas collected by the collecting nozzle and to allow the to-be-analyzed gas to pass therethrough, a liquid discharging unit configured to discharge the liquid component collected by the liquid collecting unit, and an analyzing unit configured to analyze a gas component of the to-be-analyzed gas that has passed through the liquid collecting unit.

17 Claims, 9 Drawing Sheets

(51) Int. Cl.
| | |
|---|---|
| *F01N 3/021* | (2006.01) |
| *F01N 3/04* | (2006.01) |
| *G01M 15/10* | (2006.01) |
| *G01N 21/3504* | (2014.01) |
| *G01N 21/15* | (2006.01) |
| *G01N 21/85* | (2006.01) |
| *G01N 33/00* | (2006.01) |
| *G01N 21/31* | (2006.01) |
| *G01N 21/33* | (2006.01) |
| *G01N 21/27* | (2006.01) |

(52) U.S. Cl.
CPC ......... *G01N 1/2202* (2013.01); *G01N 1/2247* (2013.01); *G01N 21/15* (2013.01); *G01N 21/31* (2013.01); *G01N 21/33* (2013.01); *G01N 21/3504* (2013.01); *G01N 21/85* (2013.01); *G01N 33/0006* (2013.01); *G01N 33/0029* (2013.01); *G01N 21/274* (2013.01); *G01N 33/004* (2013.01); *G01N 33/0011* (2013.01); *G01N 33/0037* (2013.01); *G01N 2001/227* (2013.01); *G01N 2001/2267* (2013.01); *G01N 2021/151* (2013.01); *G01N 2021/158* (2013.01); *G01N 2021/8557* (2013.01); *G01N 2021/8578* (2013.01)

(58) Field of Classification Search
CPC ....... G01N 2021/157; G01N 2021/155; G01N 1/2202; G01N 1/2258; G01N 1/2208–2214; G01M 15/102
See application file for complete search history.

(56) References Cited

U.S. PATENT DOCUMENTS

| | | | | |
|---|---|---|---|---|
| 5,621,213 | A * | 4/1997 | Barshad | G01N 21/33 250/252.1 |
| 6,290,738 | B1 * | 9/2001 | Holm | B01D 45/08 55/309 |
| 8,443,648 | B2 * | 5/2013 | Holt | G01N 1/2202 73/1.03 |
| 9,927,357 | B2 * | 3/2018 | Bitter | G01N 21/39 |
| 2002/0149774 | A1 * | 10/2002 | McAninch | G01N 21/15 356/445 |
| 2012/0192536 | A1 * | 8/2012 | Severance | B01D 45/08 55/418 |
| 2012/0236323 | A1 * | 9/2012 | Kuoppa | G01N 21/85 356/634 |
| 2013/0280132 | A1 * | 10/2013 | Maskrot | G01N 21/05 422/83 |
| 2016/0216200 | A1 * | 7/2016 | Mocnik | G01N 21/274 |

FOREIGN PATENT DOCUMENTS

| | | |
|---|---|---|
| JP | S57-066341 A | 4/1982 |
| JP | S59-006751 U | 1/1984 |
| JP | 2003-344335 A | 12/2003 |
| JP | 2013-160692 A | 8/2013 |

OTHER PUBLICATIONS

Office Action issued for counterpart Japanese Application No. 2015-109703, drafted by the Japan Patent Office dated Oct. 24, 2018.

* cited by examiner

ANALYZING APPARATUS AND EXHAUST GAS TREATING SYSTEM

The contents of the following Japanese patent application are incorporated herein by reference:
No. 2015-109703 filed on May 29, 2015.

BACKGROUND

1. Technical Field

The present invention relates to an analyzing apparatus and an exhaust gas treating system.

2. Related Art

In the conventional art, a method is known for first collecting soot and dust and liquid components from a diesel engine exhaust gas or other exhaust gases into a washing bottle and then measuring the concentration of the toxic gases such as NOx and CO contained in the exhaust gas. (See, for example, Japanese Patent Application Publication No. 2013-160692)

If the exhaust gas contains a lot of liquid components, however, the washing bottle cannot collect all of them. Furthermore, as the liquids build up in the washing bottle, the toxic substances in the exhaust gas adhere to the liquids building up in the washing bottle while the exhaust gas is passing through the washing bottle. This makes it impossible to accurately measure the concentration of the toxic substances originally contained in the exhaust gas.

SUMMARY

A first aspect of the innovations may include an analyzing apparatus for analyzing a gas component, including a collecting nozzle configured to collect a to-be-analyzed gas, a liquid collecting unit configured to collect a liquid component contained in the to-be-analyzed gas collected by the collecting nozzle and to allow the to-be-analyzed gas to pass therethrough, a liquid discharging unit configured to discharge the liquid component collected by the liquid collecting unit, and an analyzing unit configured to analyze a gas component of the to-be-analyzed gas that has passed through the liquid collecting unit.

Another aspect of the innovations may include an analyzing apparatus for analyzing a gas component, including a collecting nozzle configured to collect a to-be-analyzed gas, and an analyzing unit configured to analyze a gas component of the to-be-analyzed gas. The analyzing unit includes a light emitting unit having therein a light emitting window through which light passes, a light receiving unit having therein a light receiving window through which light passes, a gas cell unit arranged between the light emitting unit and the light receiving unit and configured to allow the to-be-analyzed gas to be introduced thereinto after passing through the liquid collecting unit, and a purge unit configured to introduce a purge gas into at least one of a region in the gas cell unit that opposes the light emitting window and a region in the gas cell unit that opposes the light receiving window.

Another aspect of the innovations may include an analyzing apparatus for analyzing a gas component, including a collecting nozzle configured to collect a to-be-analyzed gas, and an analyzing unit configured to analyze a gas component of the to-be-analyzed gas using light having a wavelength in an infrared or ultraviolet region.

In each aspect of the innovations, the collecting nozzle may have an injection opening configured to inject the to-be-analyzed gas toward the liquid collecting unit. The liquid collecting unit may include a separating and collecting unit configured to separate the liquid component contained in the to-be-analyzed gas and to allow the to-be-analyzed gas to pass therethrough, and a collecting case enclosing therein the separating and collecting unit of the liquid collecting unit and the injection opening of the collecting nozzle. The liquid discharging unit may include a discharge pipe configured to discharge the liquid component outside the collecting case.

The discharge pipe may have a feature to prevent the discharged liquid component from flowing back into the collecting case. The collecting nozzle may collect the to-be-analyzed gas passing through a flue, and the discharge pipe may discharge the liquid component into the flue.

The discharge pipe may have a reservoir unit configured to store therein the liquid component between the collecting case and the flue. The analyzing unit may include a light emitting unit having therein a light emitting window through which light passes. The analyzing unit may include a light receiving unit having therein a light receiving window through which light passes. The analyzing unit may include a gas cell unit arranged between the light emitting unit and the light receiving unit and configured to allow the to-be-analyzed gas to be introduced thereinto after passing through the liquid collecting unit. The analyzing unit may include a purge unit configured to introduce a purge gas into at least one of a region in the gas cell unit that opposes the light emitting window and a region in the gas cell unit that opposes the light receiving window.

The analyzing unit may further include a measuring unit configured to analyze the gas component of the to-be-analyzed gas based on an optical path length determined by a distance between the light emitting window and the light receiving window and a predetermined optical path length correction value. The analyzing unit may further include a flow rate control unit configured to control a flow rate of the purge gas to be introduced into the gas cell unit based on a flow rate of the to-be-analyzed gas introduced from the liquid collecting unit to the gas cell unit.

The analyzing unit may include a calibration gas introducing unit configured to introduce a calibration gas into the gas cell unit. The analyzing unit may include a measuring unit configured to measure intensity of light received by the light receiving unit for each value of a flow rate ratio between the calibration gas and the purge gas. The analyzing unit may include a storage unit configured to store therein calibration information based on the intensity of the light measured by the measuring unit in association with each value of the flow rate ratio.

The measuring unit may analyze the gas component of the to-be-analyzed gas based on (i) intensity of light received by the light receiving unit when the to-be-analyzed gas and the purge gas are introduced into the gas cell unit and (ii) the calibration information stored in the storage unit. The light emitting unit may emit light having a wavelength in an infrared or ultraviolet region.

The gas cell unit may have a plurality of inlets to introduce the to-be-analyzed gas thereinto. At least two inlets may be arranged in a nonparallel manner to an axis extending from the light emitting unit to the light receiving unit. Two of the plurality of inlets may be arranged at equal intervals in a plane that is perpendicular to the axis extending from the light emitting unit to the light receiving unit.

The analyzing apparatus may comprise two liquid collecting units. A first liquid collecting unit of the two liquid collecting units may be connected to a dust collecting unit configured to collect dust contained in the to-be-analyzed gas. A second liquid collecting unit of the two liquid collecting units may not be connected to the dust collecting unit. The analyzing apparatus may further include a selecting unit configured to introduce the to-be-analyzed gas collected by the collecting nozzle into a selected one of the first liquid collecting unit and the second liquid collecting unit.

The selecting unit may select one of the first liquid collecting unit and the second liquid collecting unit based on location information of the analyzing apparatus. The selecting unit may select one of the first liquid collecting unit and the second liquid collecting unit based on information regarding a gas source that has emitted the to-be-analyzed gas.

The to-be-analyzed gas may have passed through a scrubber apparatus. The selecting unit may select one of the first liquid collecting unit and the second liquid collecting unit based on an operational state of the scrubber apparatus.

Another aspect of the innovations may include an exhaust gas treating system including the above-described analyzing apparatus and the scrubber apparatus.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
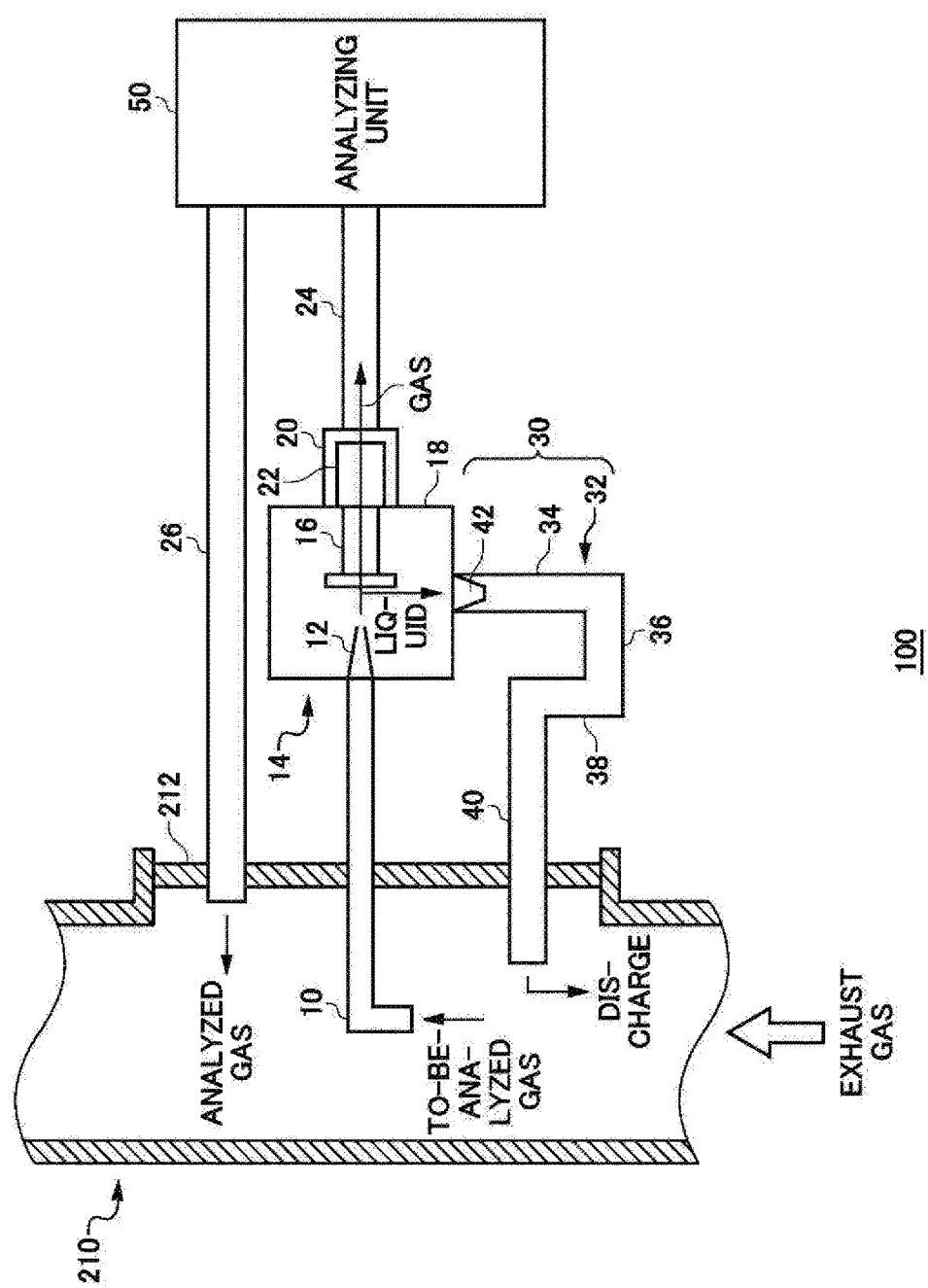
FIG. 1 shows an exemplary structure of an analyzing apparatus 100 relating to an embodiment of the present invention.

FIG. 1 shows an exemplary structure of an analyzing apparatus 100 relating to an embodiment of the present invention. The analyzing apparatus 100 is configured to analyze the concentration of a predetermined substance under measurement contained in the gas passing through a flue 210. The gas passing through the flue 210 is, for example, an exhaust gas emitted from an engine. The analyzing apparatus 100 of the present exemplary embodiment is designed to analyze the concentration of one or more types of toxic substances such as sulfur oxides, nitrogen oxides and carbon oxides contained in the exhaust gas. The analyzing apparatus 100 of the present exemplary embodiment includes a collecting nozzle 10, a liquid collecting unit 14, a dust collecting unit 20, a connection tube 24, an analyzing unit 50, a gas discharging unit 26 and a liquid discharging unit 30.

The collecting nozzle 10 is designed to collect a to-be-analyzed gas. In the present exemplary embodiment, one of the ends of the collecting nozzle 10 is inserted into the flue 210 to collect as the to-be-analyzed gas part of the exhaust gas passing through the flue 210. The collecting nozzle 10 may penetrate through a flange 212 provided on the side wall of the flue 210. The collecting nozzle 10 and other parts through which gases pass preferably have resistance against corrosion by the components contained in the gases. The collecting nozzle 10 may be formed from a glass or metal tube. The collecting nozzle 10 may collect the to-be-analyzed gas in the vicinity of the cross-sectional center of the flue 210.

The collecting nozzle 10 may collect the to-be-analyzed gas at a plurality of sites within the flue 210. The collecting nozzle 10 may collect the to-be-analyzed gas at a plurality of sites that are different in terms of the diametrical direction on the cross-section of the flue 210, and may collect the to-be-analyzed gas at a plurality of sites that are different in terms of the extending direction of the flue 210 in which the gas travels. In this way, the collected to-be-analyzed gas can have averaged gas component concentrations even when the gas components exhibit varying concentrations at different sites within the flue 210.

The liquid collecting unit 14 collects the liquid components contained in the to-be-analyzed gas collected by the collecting nozzle 10 and allows the to-be-analyzed gas to pass therethrough. The liquid collecting unit 14 of the present exemplary embodiment includes a separating and collecting unit 16 and a collecting case 18. The collecting nozzle 10 also includes an injection opening 12 to inject the collected to-be-analyzed gas towards the separating and collecting unit 16. The injection opening 12 preferably has a tapered portion in which its tubular diameter gradually decreases towards the separating and collecting unit 16. In this way, the to-be-analyzed gas can be injected towards the separating and collecting unit 16 at an improved flow velocity.

The collecting case 18 is formed so as to enclose therein the separating and collecting unit 16 and the injection opening 12 of the collecting nozzle 10. The collecting case 18 is configured to confine therein the to-be-analyzed gas injected from the injection opening 12. The collecting case 18 may be made of glass or metals.

The separating and collecting unit 16 is configured to separate at least part of the liquid components contained in the to-be-analyzed gas and allows the to-be-analyzed gas to pass therethrough. For example, the separating and collecting unit 16 separates 90% or more of the liquid components contained in the to-be-analyzed gas.

A liquid discharging unit 30 is configured to sequentially discharge the liquid components collected by the liquid collecting unit 14 to the outside of the collecting case 18. The phrase "to sequentially discharge the liquid components" means that the liquids are discharged uninterruptedly in terms of time, the liquid components are discharged at certain cycles or the liquid components are sequentially discharged each time a predetermined condition is satisfied.

The liquid discharging unit 30 may sequentially discharge the liquid components once the amount of the liquid components collected by the liquid collecting unit 14 exceeds a predetermined amount. When sequentially discharging the liquid components collected by the liquid collecting unit 14, the liquid discharging unit 30 may first discharge liquid components that have aggregated into chunks of a predetermined amount or more. For example, the liquid components collected by the liquid collecting unit 14 adhere to the surface of the separating and collecting unit 16. Once the size of the chunks of the adhering liquid components exceeds a predetermined value, the chunks of the liquid components cannot stay on the surface of the separating and collecting unit 16 and eventually fall or flow downwards under the influence of the gravity or because the to-be-analyzed gas is sprayed against the surface of the separating and collecting unit 16.

The liquid discharging unit 30 includes an opening provided at the bottom of the collecting case 18. The opening is positioned in such a manner that the liquid components fall or flow down thereon from the surface of the separating and collecting unit 16. Furthermore, the bottom of the collecting case 18 may include a slope to allow the liquid components to flow towards the opening, which is included in the liquid discharging unit 30. The liquid discharging unit 30 discharges through this opening the liquid components to the outside of the collecting case 18. The separating and collecting unit 16 may have a guide path to guide the liquids adhering to the surface thereof to the opening. The guide path may have a block section that is configured to prevent the to-be-analyzed gas injected by the collecting nozzle 10 from contacting the liquids on the guide path.

The opening may be aligned with the surface of the separating and collecting unit 16 that opposes the collecting nozzle 10.

The existence of the liquid discharging unit 30 can realize automatic liquid discharge from the collecting case 18. This feature can prevent the liquids from accumulating to a predetermined amount or more in the collecting case 18 even when manual liquid discharge from the collecting case 18 is not possible due to limitation on workspaces, for example, in the case of ships and the like.

This effect is particularly significant when the to-be-analyzed gas contains a lot of liquid components. For example, the to-be-analyzed gas contains a considerable amount of moisture when the analyzing apparatus 100 is used in an exhaust gas treating system configured to remove toxic substances such as sulfur oxides and the like from the exhaust gas by injecting mist to the exhaust gas. Even in such a case, the analyzing apparatus 100 of the present exemplary embodiment can prevent water from accumulating in large quantity in the collecting case 18 because of the automatic water discharge scheme. In this way, the present exemplary embodiment can lower the likelihood of the contact between the gas passing through the collecting case 18 and the remaining water. In addition, the present exemplary embodiment can allow the collecting case 18 to be smaller.

The liquid discharging unit 30 of the present exemplary embodiment has a discharge pipe 32 configured to discharge the liquid components to the outside of the collecting case 18. The discharge pipe 32 of the present exemplary embodiment discharges the liquids collected by the liquid collecting unit 14 into the flue 210. The flue 210 is provided at the bottom thereof with a discharge structure configured to discharge outside, from among the liquid components contained in the exhaust gas, the liquid components accumulating at the bottom of the flue 210 due to dew condensation or other reasons. The liquid components that are discharged from the discharge pipe 32 into the flue 210 are discharged to the outside of the flue 210 through the discharge structure. The discharge pipe 32 may have a structure configured to prevent the liquid components that have been discharged to the outside of the collecting case 18 from flowing back into the collecting case 18. The discharge pipe 32 may have a structure configured to prevent the exhaust gas flowing through the flue 210 from flowing into the collecting case 18 through the discharge pipe 32.

For example, a tapered funnel 42 may be provided in the vicinity of the opening of the discharge pipe 32, which is provided in the bottom of the collecting case 18. The funnel 42 has a large opening that faces the bottom of the collecting case 18 and a small opening that faces away from the collecting case 18 and is smaller in diameter than the large opening. This feature can reduce the contact area between the to-be-analyzed gas and the discharged liquids and thus prevent the gas components from being dissolved into the discharged liquids.

In the vicinity of the opening of the discharge pipe 32, a valve may be provided that is opened by the weight of the liquid components falling from the separating and collecting unit 16 and closed after the liquid components are gone. When closed, the valve blocks the liquids or gases flowing from the discharge pipe 32 to the collecting case 18. This can prevent the liquid components and the like from flowing backward.

The discharge pipe 32 of the present exemplary embodiment is divided into a first region 34, a second region 36, a third region 38 and a fourth region 40. The first region 34 has a portion extending downwards from the bottom of the collecting case 18. At least a portion of the first region 34 may extend in a direction perpendicular to the bottom of the collecting case 18. The second region 36 connects the end of the first region 34 and the end of the third region 38.

The second region 36 may have a straight portion extending in a direction parallel to the bottom of the collecting case 18, or may have an arch-like portion. The third region 38 has a portion extending upwards from the end of the second region 36. At least a portion of the third region 38 may extend in a direction perpendicular to the bottom of the collecting case 18. The fourth region 40 may have a portion that extends horizontally from the end of the third region 38 and is positioned lower than the bottom of the collecting case 18. The fourth region 40 penetrates through the flange 212 and is inserted into the flue 210. The end of the fourth region 40 that is closer to the third region 38 may be located higher than the end of the fourth region 40 that is closer to the flue 210. The fourth region 40 may be entirely located lower than the lower surface of the collecting case 18 and higher than the second region 36.

When liquids pass through the discharge pipe 32 having the above-described structure, the liquids remain at least in the second region 36. A portion of the first region 34, the second region 36 and a portion of the third region 38 together serve as a reservoir unit configured to store therein liquid components between the collecting case 18 and the flue 210. The stored liquids seal the discharge pipe 32, which can prevent gases from passing through the discharge pipe 32. In addition, since the fourth region 40 is located lower than the lower surface of the collecting case 18, the liquid components can be prevented from flowing back into the collecting case 18.

The dust collecting unit 20 is configured to collect the dust contained in the to-be-analyzed gas that has passed through the liquid collecting unit 14. The dust collecting unit 20 includes a filter 22 provided within a case. The filter 22 has, for example, a fiber portion that is configured to allow the to-be-analyzed gas to pass therethrough. The filter 22 is configured to collect the dust contained in the to-be-analyzed gas by causing the dust to adhere to the fiber portion.

The connection tube 24 is configured to transport to the analyzing unit 50 the to-be-analyzed gas that has passed through the dust collecting unit 20. The connection tube 24 may be provided with a pump that is configured to suction the gas injected from the collecting nozzle 10 and eject the suctioned gas toward the analyzing unit 50. The connection tube 24 may be heated to prevent the liquid components contained in the to-be-analyzed gas passing therethrough from forming water droplets. Likewise, the dust collecting unit 20 and a gas cell unit 55, which will be described later, may be also heated.

The analyzing unit 50 is configured to analyze the gas components of the to-be-analyzed gas that has passed through the liquid collecting unit 14 and the dust collecting unit 20. The analyzing unit 50 applies light having a predetermined wavelength component to the to-be-analyzed gas. The analyzing unit 50 may calculate the concentration of a substance under measurement based on how much the predetermined wavelength component is absorbed by the to-be-analyzed gas. After introduced into the analyzing unit 50, the gas travels through the analyzing unit 50 and then returns to the inside of the flue 210 via the gas discharging unit 26. The gas discharging unit 26 of the present exemplary embodiment penetrates through the flange 212 of the flue 210.

The analyzing apparatus 100 of the present exemplary embodiment is configured to analyze the gas components of the to-be-analyzed gas after collecting and removing the liquid components contained in the to-be-analyzed gas. As a consequence, the analyzing apparatus 100 of the present exemplary embodiment can reduce the influence of the liquid components and thus accurately analyze the gas components. In addition, by sequentially discharging the liquid components that have been collected by the liquid collecting unit 14 to the outside of the collecting case 18 as described above, the analyzing apparatus 100 of the present exemplary embodiment can prevent the liquid components from building up in the collecting case 18. In this manner, the analyzing apparatus 100 of the present exemplary embodiment can lower the likelihood of the contact between the to-be-analyzed gas and the liquid accumulating in the collecting case 18. This can prevent the components under measurement contained in the to-be-analyzed gas from being absorbed by the liquids accumulating in the collecting case 18 and the analyzing apparatus 100 of the present exemplary embodiment can thus achieve accurate analysis of the gas components of the to-be-analyzed gas. In addition, since the collecting case 18 can be small, the analyzing apparatus 100 can be smaller.

Figure 2:
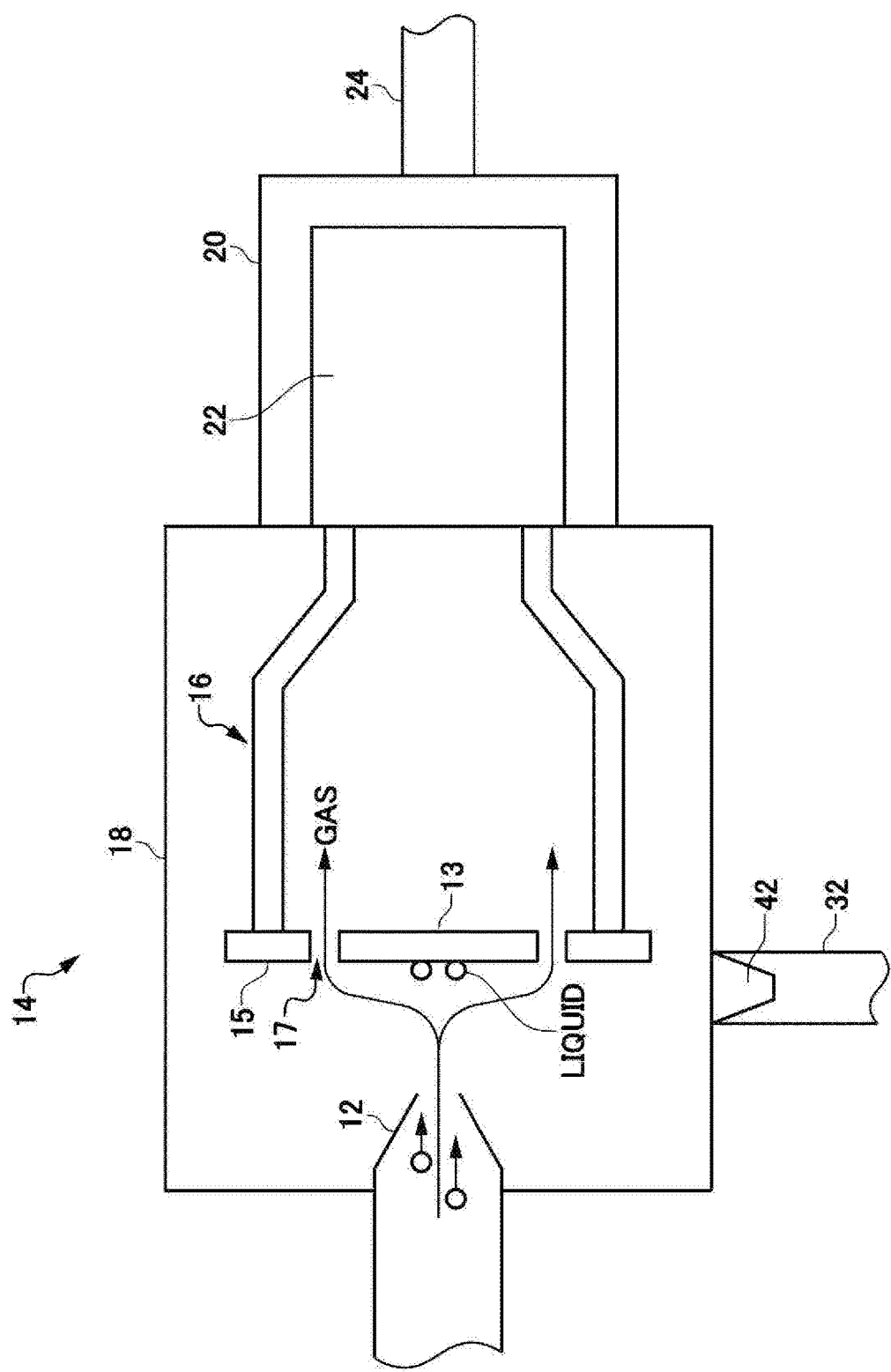
FIG. 2 shows an exemplary structure of a liquid collecting unit 14 and a dust collecting unit 20.

FIG. 2 shows an exemplary structure of the liquid collecting unit 14 and the dust collecting unit 20. The separating and collecting unit 16 of the present exemplary embodiment includes a separating plate 15. The separating plate 15 opposes the injection opening 12 of the collecting nozzle 10. The separating plate 15 includes a plate-like portion 13 positioned so as to oppose the injection opening 12 and a gas flow hole 17 surrounding the plate-like portion 13.

The to-be-analyzed gas is injected from the injection opening 12 of the collecting nozzle 10 toward the plate-like portion 13. The gas components contained in the to-be-analyzed gas travel to the gas flow hole 17 surrounding the plate-like portion 13 and pass through the gas flow hole 17. On the other hand, the liquid components contained in the to-be-analyzed gas collide with and adhere to the plate-like portion 13 due to their inertia, because of their larger mass than the gas components' mass. In this manner, the liquid components contained in the to-be-analyzed gas are collected.

The separating plate 15 is preferably made of a material resistant against corrosion by the to-be-analyzed gas containing liquid components. For example, the separating plate 15 is made of glass. The entire liquid collecting unit 14 may be made of glass. The collecting case 18 may be also made of glass.

As described above, after having passed through the liquid collecting unit 14, the to-be-analyzed gas is introduced into the dust collecting unit 20. The filter 22 of the dust collecting unit 20 collects the soot, dust and the like contained in the to-be-analyzed gas. The filter 22 is preferably replaceable. In order to make the filter 22 replaceable, the dust collecting unit 20 may be configured such that a portion of the wall of the case housing the filter 22 therein may be openable and closeable, or removable. On the other hand, the separating and collecting unit 16 may be fixed to the collecting case 18. The collecting case 18 may be formed as a single piece and be configured such that a portion of its wall is not openable and closeable, or removable.

Figure 3:
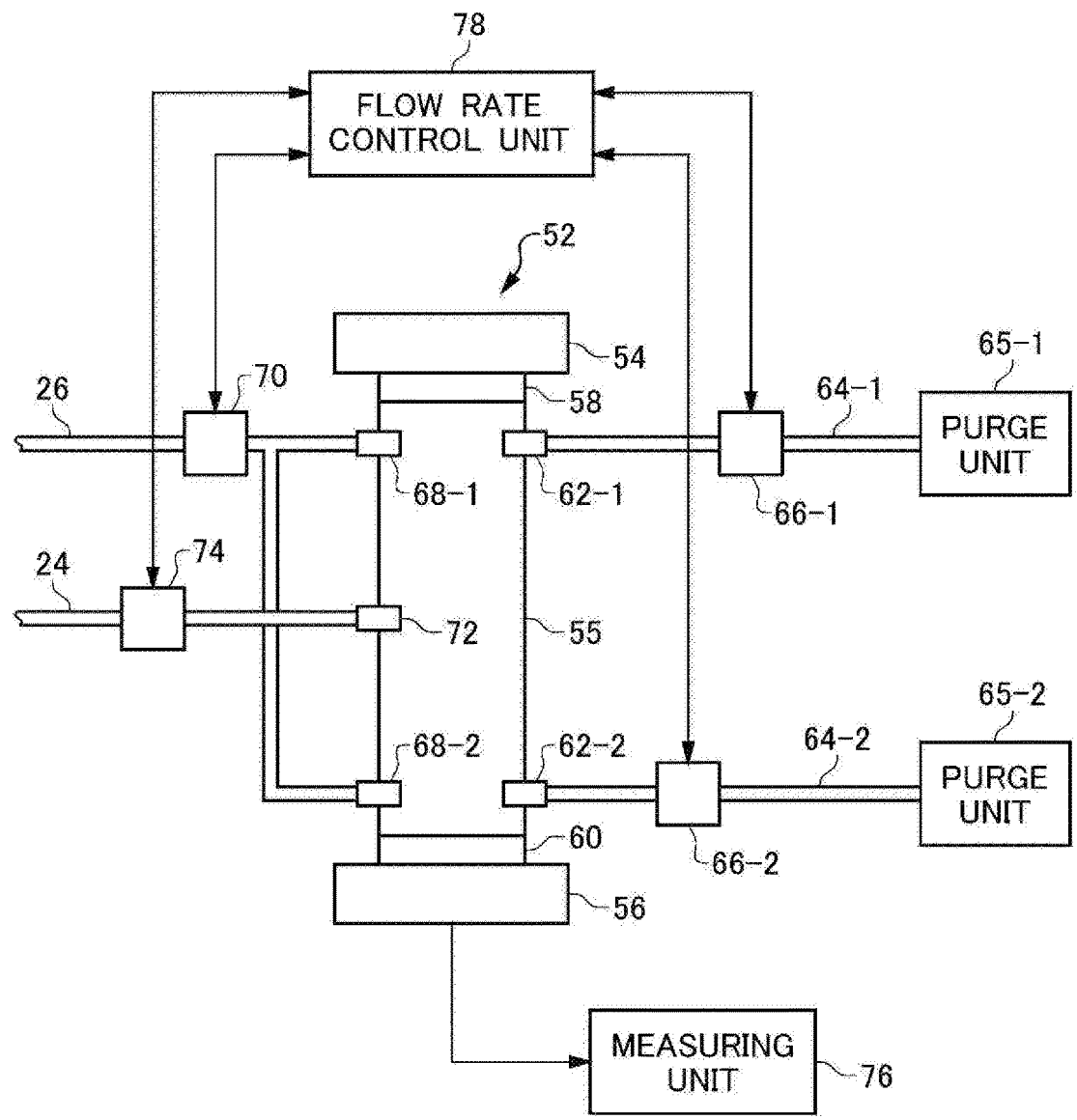
FIG. 3 shows an exemplary structure of an analyzing unit 50.

FIG. 3 shows an exemplary structure of the analyzing unit 50. The analyzing unit 50 of the present exemplary embodiment includes a spectroscopic measuring unit 52, a measuring unit 76, a flow rate control unit 78, two purge units 65, two purge tubes 64, two purge pumps 66, a gas discharge pump 70, and a gas introducing pump 74. The flow rate control unit 78 is configured to control the flow rates of the respective gases. The flow rate control unit 78 of the present exemplary embodiment controls the flow rates of the respective gases by controlling the respective pumps.

The spectroscopic measuring unit 52 is configured to analyze the gas components contained in the to-be-analyzed gas based on optical absorption spectra observed when light having a predetermined wavelength is applied to the to-be-analyzed gas. The spectroscopic measuring unit 52 includes a light emitting unit 54, a light emitting window 58, a light receiving unit 56, a light receiving window 60 and a gas cell unit 55.

The light emitting unit 54 applies light having a predetermined wavelength to the light receiving unit 56. The light emitting unit 54 may apply laser light or light having a predeminted wavelength range. The light emitting unit 54 of the present exemplary embodiment applies laser light.

The gas cell unit 55 is provided between the light emitting unit 54 and the light receiving unit 56, and the to-be-analyzed gas is introduced into the gas cell unit 55 after passing through the liquid collecting unit 14. The gas cell unit 55] is preferably heated to prevent the liquid components contained in the to-be-analyzed gas from condensing into droplets. The gas cell unit 55 is shaped like a tube to allow light and gases to pass therethrough. The gas cell unit 55 has in the side wall thereof a to-be-analyzed gas inlet 72 to introduce the to-be-analyzed gas into the gas cell unit 55. The to-be-analyzed gas inlet 72 of the present exemplary embodiment is arranged in the middle of the gas cell unit 55 in the height direction.

Furthermore, the gas cell unit 55 has in the side wall thereof gas outlets 68 to discharge the gases from the gas cell unit 55. The gas cell unit 55 of the present exemplary embodiment has a gas outlet 68-1 arranged between the light emitting unit 54 and the to-be-analyzed gas inlet 72 and a gas outlet 68-2 arranged between the light receiving unit 56 and the to-be-analyzed gas inlet 72. The gas outlet 68-1 is preferably provided in the vicinity of the light emitting unit 54 and the gas outlet 68-2 is preferably provided in the vicinity of the light receiving unit 56. This allows the to-be-analyzed gas to be distributed in the height direction of the gas cell unit 55.

The light emitting window 58 opposes the light emitting unit 54 and transmits the light emitted from the light emitting unit 54. The light emitting window 58 of the present exemplary embodiment is provided between the light emitting unit 54 and the gas outlet 68-1 in the height direction of the gas cell unit 55. The light emitting window 58 may be in contact with the light emitting surface of the light emitting unit 54.

The light receiving window 60 opposes the light receiving unit 56 and transmits the light emitted from the light emitting unit 54 toward the light receiving unit 56. The light receiving window 60 of the present exemplary embodiment is provided between the light receiving unit 56 and the gas outlet 68-2 in the height direction of the gas cell unit 55. The light receiving window 60 may be in contact with the light receiving surface of the light receiving unit 56.

With the above-described configurations, the light emitted from the light emitting unit 54 is absorbed in a manner determined by the optical absorption spectra unique to the respective substances contained in the to-be-analyzed gas in the gas cell unit 55. The light receiving unit 56 receives the light having passed through the to-be-analyzed gas.

The measuring unit 76 analyzes the gas components of the to-be-analyzed gas based on the light emission intensity at the light emitting unit 54 and the light reception intensity at the light receiving unit 56. The light emission intensity at the light emitting unit 54 may be calculated based on the control information for the light emitting unit 54. Alternatively, the gas cell unit 55 is vacuumed, the light emitting unit 54 is caused to emit light, and the light reception intrensity is measured at the light receiving unit 56, so that the measured light reception intensity in this manner may be used as the light emission intensity at the light emitting unit 54. Alternatively, the gas cell unit 55 is filled with air or nitrogen, the light emitting unit 54 is caused to emit light, and the light reception intensity is measured at the light receiving unit 56, so that the measured light reception intensity may be used as the light emission intensity at the light emitting unit 54.

The measuring unit 76 may calculate the concentration of a substance under measurement contained in the to-be-analyzed gas based on the ratio between the light emission intensity and the light reception intensity at the wavelength corresponding to the substance under measurement.

The light emitting unit 54 emits light having a wavelength corresponding to a substance to be analyzed.

Here, the to-be-analyzed gas that has passed through the liquid collecting unit 14 may still contain liquid components having a minute particle size. In order to reduce the influence of such liquid components, the light emitting unit 54 preferably emits light having a wavelength at which the amount of the light absorbed by the liquid components is smaller than the amount of the light absorbed by the substance under measurement. The amount of the light absorbed denotes the amount of the light absorbed while the light travels through the gas cell unit 55. Here, the wavelength may be selected such that the amount of the light absorbed by the liquid components is 20% or lower, or 10% or lower of the amount of the light absorbed by the substance under measurement.

In addition, the light emitting unit 54 preferably emits light having a wavelength at which the absorbance per unit volume of the liquid components is lower than a predetermined value and the absorbance per unit volume of the substance under measurement is higher than a predetermined value. For example, the light emitting unit 54 emits light having a wavelength that is equal to one of the peak wavelengths in the optical absorption spectrum of the substance under measurement and at which the optical absorbance of the liquid components is 50% or lower of the maximum absorbance in the optical absorption spectrum of the liquid components. The wavelength may be selected such that the optical absorbance of the liquid components is 30% or lower of the maximum absorbance in the optical absorption spectrum of the liquid components.

An example is taken where the liquid components are water and the substance to be measured is a sulfur oxide or nitrogen oxide. The light emitting unit 54 emits light having a wavelength in the infrared or ultraviolet region. More specifically, when the substance to be measured is $SO_2$, the light emitting unit 54 emits light having a wavelength in the vicinity of 7 μm. When the substance to be measured is $NO_2$, the light emitting unit 54 emits light having a wavelength in the vicinity of 6 μm. Since the light emitting unit 54 is controlled to emit light having such wavelengths, the analyzing apparatus 100 of the present exemplary embodiment can reduce the influence of the liquid components that may remain in the to-be-analyzed gas that has passed through the liquid collecting unit 14 to analyze the to-be-analyzed gas.

When there are a plurality of types of substances to be measured, the light emitting unit 54 may emit light rays having wavelengths respectively corresponding to the plurality of types of substances in a time-sharing manner. Alternatively, the light emitting unit 54 may emit light having a plurality of wavelengths respectively corresponding to the plurality of types of substances. In this case, the light receiving unit 56 is preferably configured to be capable of separately measuring the intensity of the light at each of the wavelengths.

The light emitting unit 54 may vary the wavelength of the light to emit based on the temperature of the to-be-analyzed gas introduced into the gas cell unit 55. When the peak wavelengths of the optical absorption spectrum of the substance under measurement vary depending on the temperature, the light emitting unit 54 may store in advance thereon, in association with each substance under measurement, the information relating to the wavelength to be used for each temperature level. Alternatively, the analyzing apparatus 100 may be configured to control the temperature of the connection tube 24 in such a manner that the temperature of the to-be-analyzed gas introduced into the gas cell unit 55 stays constant.

The gas cell unit 55 has in the side wall thereof purge gas inlets 62 to introduce a purge gas into the gas cell unit 55. The gas cell unit 55 of the present exemplary embodiment includes a purge gas inlet 62-1 corresponding to the gas outlet 68-1 and a purge gas inlet 62-2 corresponding to the gas outlet 68-2. Each of the purge gas inlets 62 may be positioned so as to oppose a corresponding one of the gas outlets 68.

The purge units 65 are configured to introduce a purge gas into at least one of the region in the gas cell unit 55 opposing the light emitting window 58 and the region in the gas cell unit 55 opposing the light receiving window 60. In the analyzing unit 50 of the present exemplary embodiment, the purge unit 65-1 introduces the purge gas into the region in the gas cell unit 55 opposing the light emitting window 58 through the purge tube 64-1 and the purge gas inlet 62-1. Likewise, the purge unit 65-2 introduces the purge gas into the region in the gas cell unit 55 opposing the light receiving window 60 through the purge tube 64-2 and the purge gas inlet 62-2. It is preferable that at least part of the purge gas contacts the light emitting window 58 and the light receiving window 60.

The purge gas preferably has a lower dust density than the to-be-analyzed gas that has passed through the dust collecting unit 20 and, at the same time, exhibits lower absorbance than a predetermined value for the light emitted from the light emitting unit 54. The purge gas may be a nitrogen gas or air.

The purge gas introduced into the gas cell unit 55 is sequentially discharged through the gas outlets 68. In this manner, the purge gas continuously flow into the region opposing the light emitting window 58 and the region opposing the light receiving window 60. This can accordingly prevent the dust contained in the to-be-analyzed gas from adhering to the light emitting window 58 and the light receiving window 60.

Figure 4:
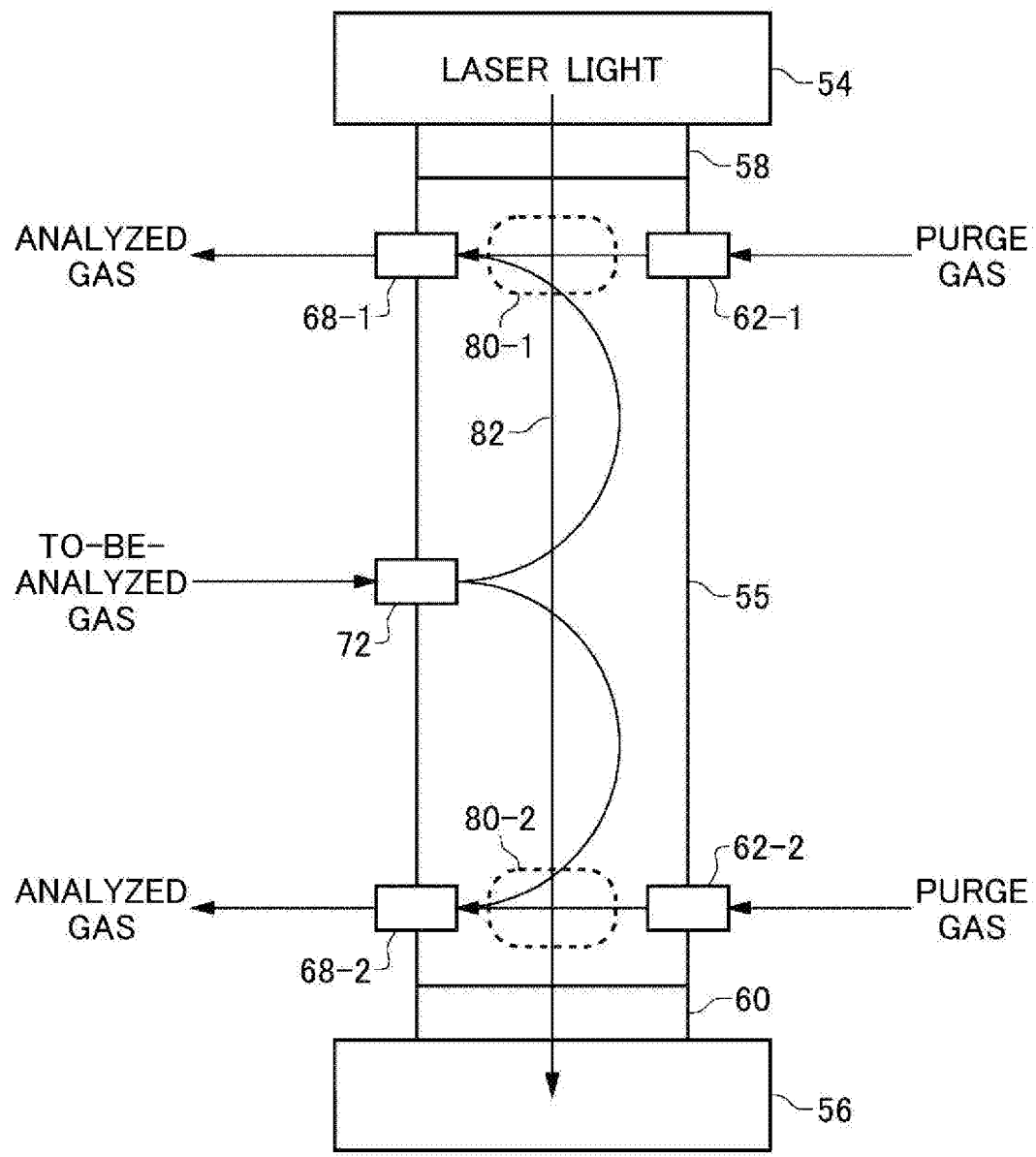
FIG. 4 schematically shows the flows of gases in a spectroscopic measuring unit 52.

FIG. 4 schematically shows the flows of the gases in the spectroscopic measuring unit 52. After introduced into the gas cell unit 55 through the to-be-analyzed gas inlet 72, the to-be-analyzed gas moves within the gas cell unit 55 toward the gas outlets 68. Since the gas outlets 68 are positioned in the vicinity of the light emitting unit 54 and the light receiving unit 56 in the present exemplary embodiment, the to-be-analyzed gas moves toward the light emitting unit 54 and the light receiving unit 56. Accordingly, the to-be-analyzed gas is distributed in the height direction of the gas cell unit 55 in a predetermined concentration.

In addition, the purge gas introduced through the purge gas inlets 62 is also suctioned toward the gas outlets 68. Since each of the purge gas inlets 62 is located at the same height as a corresponding one of the gas outlets 68 in the vicinity of the light emitting window 58 or light receiving window 60, the purge gas flows at the height of the inlets 62 and outlets 68 along the light emitting window 58 or light receiving window 60. This configuration can reduce the amount of the to-be-analyzed gas diffusing in the region 80-1 opposing the light emitting window 58 and in the region 80-2 opposing the light receiving window 60. Accordingly, the dust can be prevented from adhering to the light emitting window 58 and the light receiving window 60.

The purge gas inlets 62 and the gas outlets 68 are preferably positioned so that the purge gas flows in the regions 80-1 and 80-2 on an optical path 82 through which the laser light travels. For example, when the laser light travels through the optical path 82 at the center of the gas cell unit 55, each of the purge gas inlets 62 may be positioned on the side wall of the gas cell unit 55 so as to oppose a corresponding one of the gas outlets 68. In other words, each of the purge gas inlets 62 and a corresponding one of the gas outlets 68 may be arranged at the respective ends of the diameter line of the gas cell unit 55.

The light emitting unit 54 emits laser light having a predetermined wavelength while the to-be-analyzed gas and the purge gas is continuously introduced and discharged into/from the gas cell unit 55. The intensity $P_{56}$ of the light received by the light receiving unit 56 is defined by the following equation.

$$P_{56} = P_{54} \cdot \exp(-\varepsilon \cdot c \cdot L) \qquad \text{Equation 1}$$

Here, $P_{54}$ denotes the intensity of the laser light emitted from the light emitting unit 54, $\varepsilon$ denotes the optical absorption coefficient of the component under measurement at the wavelength of the laser light, c denotes the concentration of the component under measurement contained in the to-be-analyzed gas through which the laser light travels, and L denotes the length of the optical path through which the laser light travels in the to-be-analyzed gas and is typically equal to the length of the gas cell unit 55.

Since the values of the light emission intensity $P_{54}$, the optical absorption coefficient $\varepsilon$ and the optical path length L (the length of the gas cell unit 55) are known, the concentration c of the component under measurement contained in the to-be-analyzed gas can be calculated by measuring the light reception intensity $P_{56}$. Here, if the purge gas is controlled to continuously flow along the light emitting window 58 and the light receiving window 60, the to-be-analyzed gas cannot easily enter the regions 80-1 and 80-2. As a result, the to-be-analyzed gas eventually disappear from the regions 80-1 and 80-2, which shortens the effective optical path length L. In other words, the optical path length L through which the laser light travels within the to-be-analyzed gas is shorter than the length of the gas cell unit 55 by the lengths of the regions 80-1 and 80-2, into which the to-be-analyzed gas cannot enter.

The measuring unit 76 preferably corrects the optical path length L according to the lengths of the regions 80-1 and 80-2. The lengths of the regions 80-1 and 80-2 depend on the flow rate ratio between the to-be-analyzed gas and the purge gas. The measuring unit 76 may vary the value of the optical path length L depending on the gas flow rate ratio. Alternatively, the measuring unit 76 may control the flow rate of the purge gas in such a manner that the gas flow rate ratio stays constant. In this case, the measuring unit 76 can use a fixed value as the corrected value of the optical path length L.

When it is desired that the above-described gas flow rate ratio is controlled to be constant, the flow rate control unit 78 controls the flow rate of the purge gas introduced into the gas cell unit 55 based on the flow rate of the to-be-analyzed gas introduced into the gas cell unit 55. The flow rate control unit 78 of the present exemplary embodiment controls the flow rate of the purge gas by controlling the purge pumps 66, which are configured to regulate the gas flow rates in the purge tubes 64. The flow rate control unit 78 may set the flow rates in the two purge pumps 66 to the same value. The flow rate control unit 78 may detect the flow rate of the to-be-analyzed gas introduced into the gas cell unit 55 with reference to the control information at the gas introducing pump 74, which is configured to regulate the gas flow rate in the connection tube 24. The flow rate control unit 78 may also detect the flow rate of the to-be-analyzed gas using a flow meter provided in the connection tube 24.

In addition, the flow rate control unit 78 may control the gas discharge pump 70, which is configured to regulate the gas flow rate in the gas discharging unit 26, based on the total of the flow rates of the purge gas and the to-be-analyzed gas introduced into the gas cell unit 55. For example, the flow rate control unit 78 controls the gas discharge pump 70 in such a manner that the total of the flow rates of the purge gas and the to-be-analyzed gas becomes equal to the flow rate of the analyzed gas discharged from the gas discharging unit 26. In addition, the gas discharge pump 70 prevents the exhaust gas from being introduced into the gas cell unit 55 from the flue 210 through the gas discharging unit 26.

The flow rate control unit 78 may control the flow rate of the purge gas to be zero. For example, when it is desired that the gas components are analyzed highly accurately, for example, in a performance test of an exhaust gas treating apparatus provided before the flue 210, the flow rate control unit 78 controls the flow rate of the purge gas to be zero. In this case, the measuring unit 76 may use the length of the gas cell unit 55 as the optical path length L.

The to-be-analyzed gas inlet 72 is preferably configured to introduce the to-be-analyzed gas into the gas cell unit 55 in such a manner that the concentration distribution of the to-be-analyzed gas is as uniform as possible within the plane that is perpendicular to the optical path 82. This feature can reduce the errors of the analyses of the gas components, which are caused, for example, by misalignment of the optical path 82 of the laser light.

Figure 5:
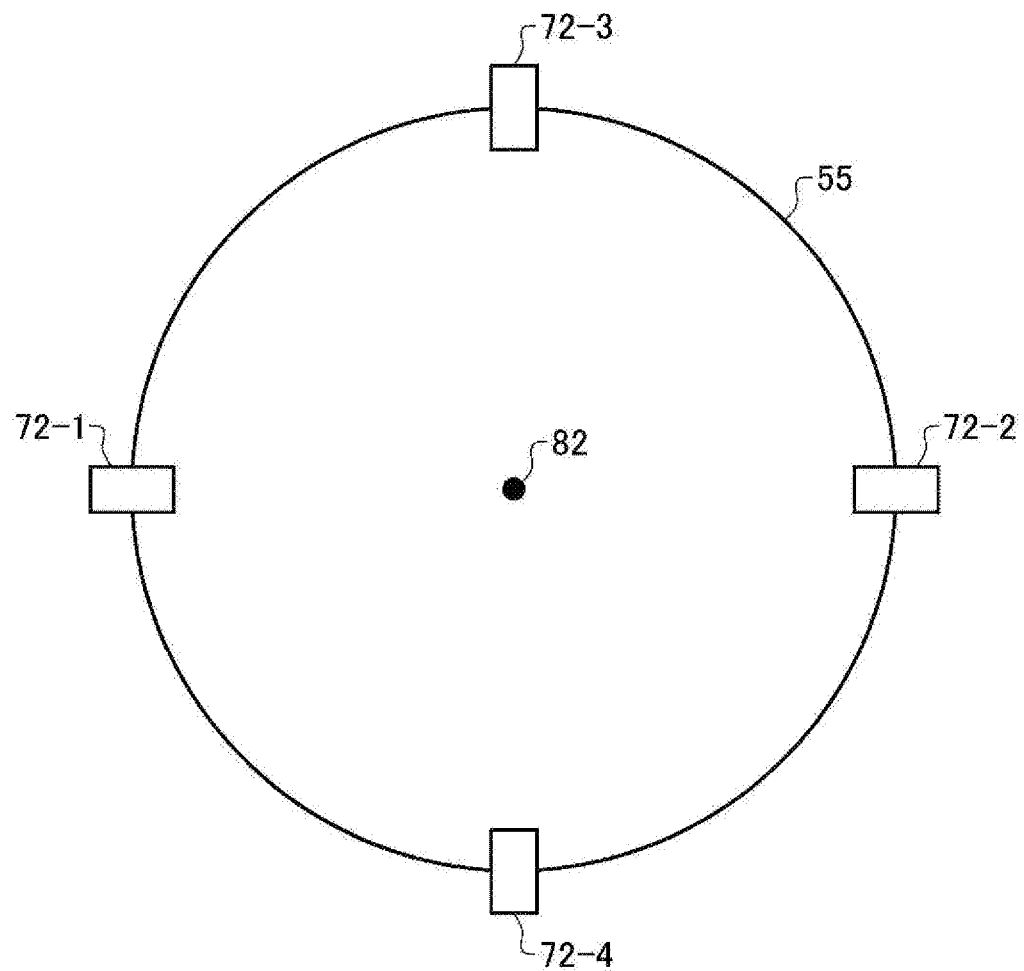
FIG. 5 shows, as an example, how to-be-analyzed gas inlets 72 are arranged.

FIG. 5 shows, as an example, how the to-be-analyzed gas inlets 72 are arranged. FIG. 5 shows the gas cell unit 55 seen from the direction parallel to the optical path 82. The gas cell unit 55 of the present exemplary embodiment has a plurality of to-be-analyzed gas inlets 72. The respective to-be-analyzed gas inlets 72 are preferably located at the same height.

The plurality of to-be-analyzed gas inlets 72 are arranged in a nonparallel manner to the axis extending from the light emitting unit 54 to the light receiving unit 56 (in the present exemplary embodiment, the axis coincides with the optical path 82). In other words, the plurality of to-be-analyzed gas inlets 72 are positioned so as not to overlap each other when the gas cell unit 55 is seen from the direction parallel to the optical path 82. The plurality of to-be-analyzed gas inlets 72 are preferably arranged at equal intervals in the side wall of the gas cell unit 55 in the plane that is perpendicular to the optical path 82 shown in FIG. 5.

For example, when two to-be-analyzed gas inlets 72 are provided, the to-be-analyzed gas inlets 72 are positioned so as to oppose each other with the optical path 82 being sandwiched therebetween. When four to-be-analyzed gas inlets 72 are provided, the to-be-analyzed gas inlets 72 are positioned in such a manner that an angle of 90 degrees is formed between the straight lines connecting the respective to-be-analyzed gas inlets 72 and the center of the gas cell unit 55. Such arrangement can achieve a more uniform concentration distribution for the to-be-analyzed gas within the plane that is perpendicular to the optical path 82.

Here, a plurality of gas outlets 68-1, a plurality of gas outlets 68-2, a plurality of purge gas inlets 62-1 and a plurality of purge gas inlets 62-2 may be also possible. It should be, however, noted that the gas outlets 68-1 are preferably positioned so as to oppose the purge gas inlets 62-1. In addition, the gas outlets 68-2 are also preferably positioned so as to oppose the purge gas inlets 62-2. As an example, if arranged as shown in FIG. 5, the gas outlets 68-1 may be arranged at the positions of the to-be-analyzed gas inlets 72-1 and 72-4, and the purge gas inlets 62-1 may be arranged at the positions of the to-be-analyzed gas inlets 72-2 and 72-3.

Figure 6:
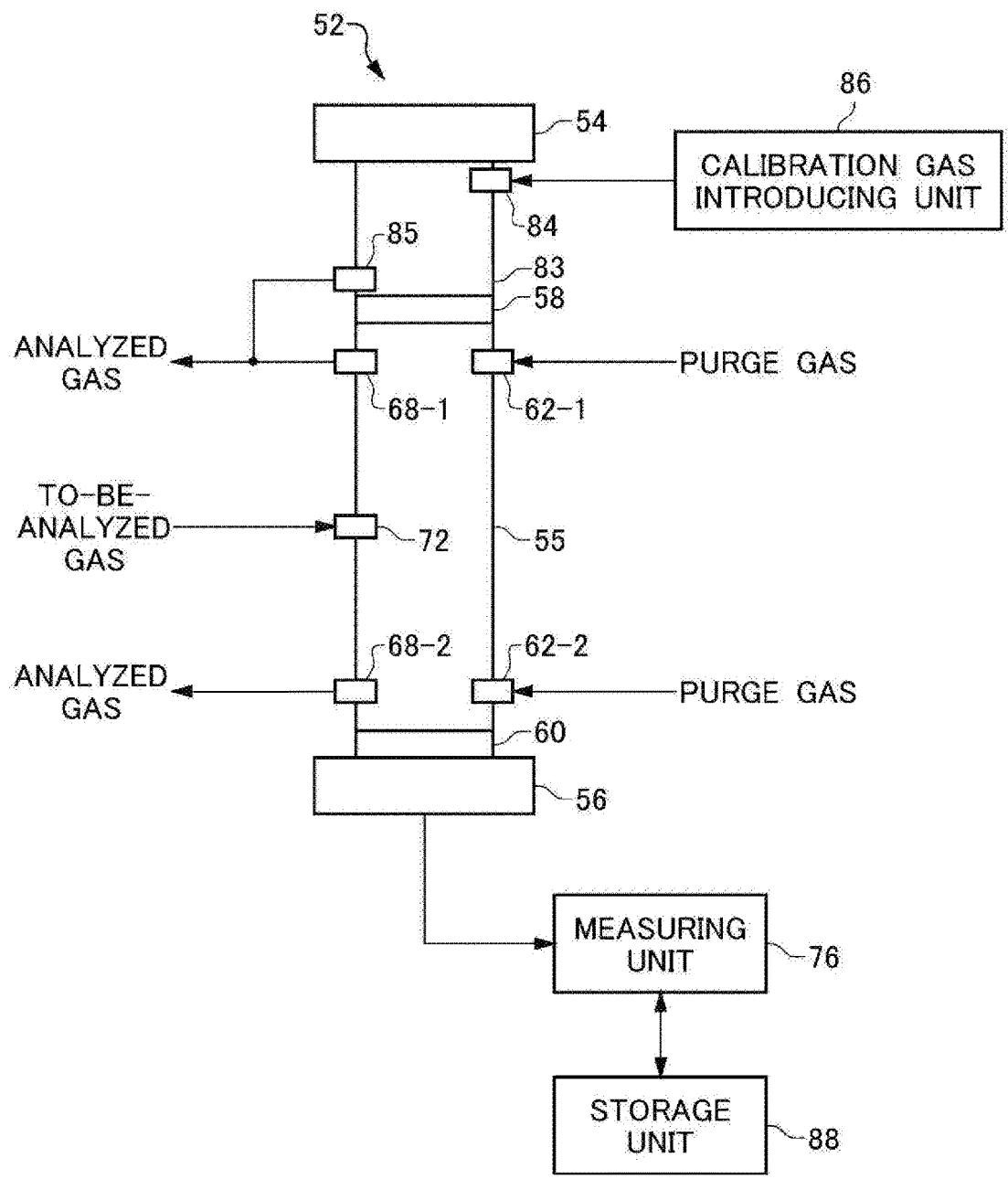
FIG. 6 shows another exemplary structure of the analyzing unit 50.

FIG. 6 shows another exemplary structure of the analyzing unit 50. The analyzing unit 50 of the present exemplary embodiment includes, in addition to the components of the analyzing unit 50 described with reference to FIGS. 3 to 5, a calibration gas introducing unit 86, a calibration gas inlet 84, a calibration gas outlet 85 and a storage unit 88. Here, FIG. 6 does not show the tubes transporting the respective gases, the pumps to regulate the flow rates of the respective gases, and the flow rate control unit 78.

The analyzing unit 50 may perform calibration on the analyzing unit 50 using a calibration gas at a predetermined timing. For example, the analyzing unit 50 may perform calibration at predetermined time intervals. When performing calibration, the analyzing unit 50 controls the gas introducing pump 74 to prevent the to-be-analyzed gas from being introduced into the gas cell unit 55.

The calibration gas introducing unit 86 introduces the calibration gas into the gas cell unit 55. The calibration gas contains, in a predetermined concentration, the substance under measurement contained in the to-be-analyzed gas. The calibration gas preferably contains as little dust as the purge gas. The calibration gas inlet 84 is provided in the side wall of the gas cell unit 55. The gas cell unit 55 of the present exemplary embodiment has an extension unit 83 between the light emitting unit 54 and the light emitting window 58. The extension unit 83 preferably has the same diameter as a portion of the gas cell unit 55 that extends between the light emitting window 58 and the light receiving window 60. The extension unit 83 is separated by the light emitting window 58 from the other region of the gas cell unit 55.

The calibration gas inlet 84 and the calibration gas outlet 85 are provided in the side wall of the extension unit 83 of the gas cell unit 55. The calibration gas inlet 84 may be provided in the vicinity of the light emitting unit 54. The calibration gas outlet 85 may be provided in the vicinity of the light emitting window 58. The calibration gas outlet 85 may be connected to the gas discharging unit 26. When calibration is performed, it may not be necessary to introduce the purge gas into the gas cell unit 55.

The flow rate control unit 78 may control the flow rate of the calibration gas to be similar to the flow rate of the to-be-analyzed gas during normal operation. When the purge gas is introduced into the gas cell unit 55 during calibration, the flow rate control unit 78 may control the flow rates of the calibration gas and the purge gas in such a manner that the flow rate ratio between the calibration gas and the purge gas becomes similar to the flow rate ratio between the to-be-analyzed gas and the purge gas during normal operation.

The measuring unit 76 measures the intensity of the light received by the light receiving unit 56 while the calibration gas is being introduced into the gas cell unit 55. The measuring unit 76 stores in the storage unit 88 the intensity ratio between the light emitted from the light emitting unit 54 and the light received by the light receiving unit 56 in association with the concentration of the substance under measurement contained in the calibration gas, as first calibration information.

The calibration gas introducing unit 86 may vary the concentration of the substance under measurement contained in the calibration gas. In this case, the storage unit 88 stores therein the above-described first calibration information for each level of the concentration of the substance under measurement. The measuring unit 76 refers to the first calibration information stored in the storage unit 88 to detect the concentration of the substance under measurement based on the light intensity ratio detected while the to-be-analyzed gas is being introduced into the gas cell unit 55. In this manner, the concentration of the substance under measurement in the to-be-analyzed gas can be detected.

The measuring unit 76 may correct the concentration of the substance under measurement in the to-be-analyzed gas based on the ratio between the optical path length L during normal operation and the length of the extension unit 83. As expressed in Equation 1, the light reception intensity at the light receiving unit 56 depends on the length of the optical path along which the laser light travels in the calibration gas or to-be-analyzed gas. Accordingly, when the length of the extension unit 83 is different from the optical path length L during normal operation, the measuring unit 76 corrects the measured concentration of the substance under measurement contained in the to-be-analyzed gas, based on the ratio between the optical path length L during normal operation and the length of the extension unit 83.

The extension unit 83 may have the same length as a portion of the gas cell unit 55 that extends between the light emitting window 58 and the light receiving window 60. In this case, the optical path length L during normal operation is substantially the same as the length of the extension unit 83.

The calibration gas introducing unit 86 may introduce the calibration gas into the gas cell unit 55 through the to-be-analyzed gas inlet 72. In this case, the gas cell unit 55 does not have the extension unit 83. Accordingly, the optical path length during calibration can be the same as the optical path length L during normal operation. The connection tube 24 may be provided with a selecting unit to select one of the to-be-analyzed gas and the calibration gas and supply the selected gas to the to-be-analyzed gas inlet 72.

The flow rate control unit 78 may vary the ratio of the purge gas flow rate to the calibration gas flow rate in order to obtain calibration information. The flow rate control unit 78 may fix the flow rate of the calibration gas and vary the flow rate of the purge gas.

For example, the measuring unit 76 measures the intensity of the light received by the light receiving unit 56 in association with each value of the flow rate ratio between the calibration gas and the purge gas. The measuring unit 76 calculates the intensity ratio between the light emitted from the light emitting unit 54 and the light received by the light receiving unit 56. The storage unit 88 stores therein second calibration information indicating the measured light intensity ratio in association with each value of the gas flow rate ratio.

Figure 7:
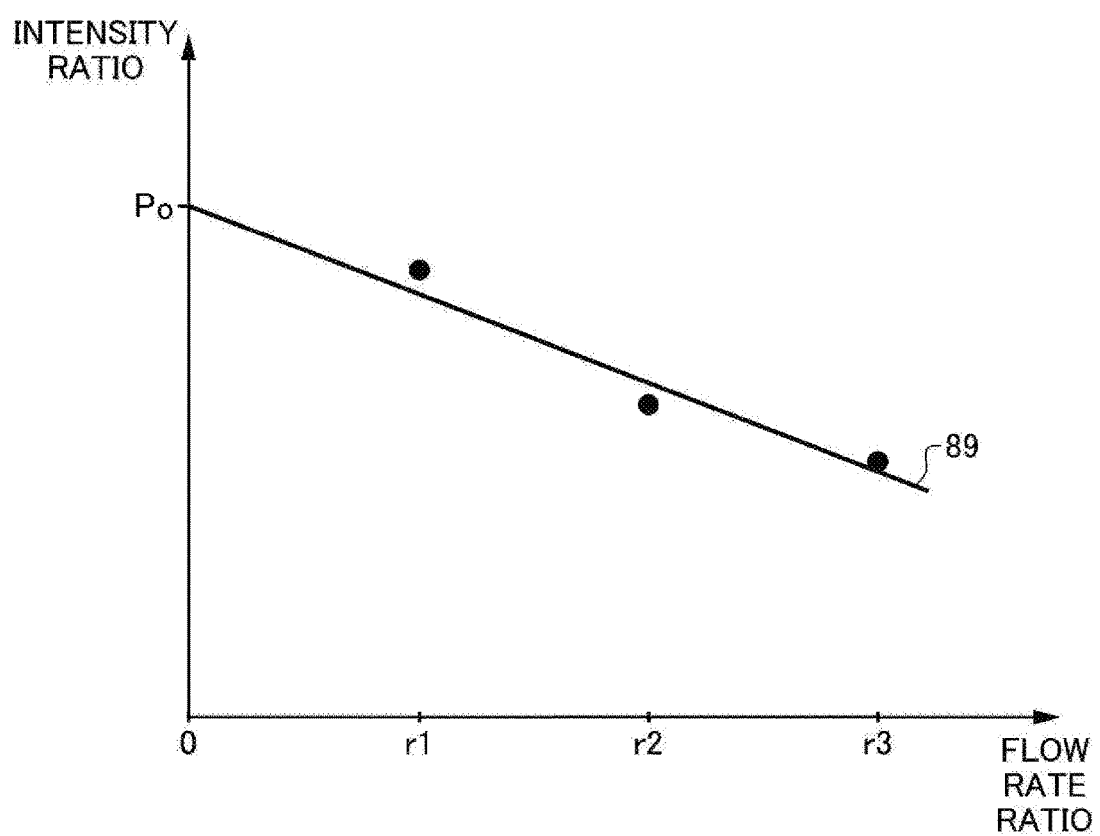
FIG. 7 shows the relation between the flow rate ratio between a calibration gas and a purge gas and the intensity ratio between the light emitted from a light emitting unit 54 and the light received by a light receiving unit 56.

FIG. 7 shows the relation between the flow rate ratio between the calibration gas and the purge gas and the intensity ratio between the light emitted from the light emitting unit 54 and the light received by the light receiving unit 56. The flow rate ratio represented by the horizontal axis is calculated by dividing the flow rate of the purge gas by the flow rate of the calibration gas. Here, it is assumed that the flow rate of the calibration gas and the concentrations of the respective substances contained in the calibration gas are fixed. In other words, as the value on the horizontal axis decreases, the flow rate of the purge gas decreases.

The intensity ratio represented by the vertical axis is calculated by dividing the intensity of the light emitted from the light emitting unit 54 by the intensity of the light received by the light receiving unit 56. In other words, as the value on the vertical axis decreases, the absorbance of the light through the calibration gas and the purge gas increases.

The purge gas is preferably selected not to absorb the light emitted from the light emitting unit 54 but may possibly exhibit non-zero absorption. If such is the case, the purge gas causes errors in the measurements of the gas components that are taken with the to-be-analyzed gas and the purge gas being introduced into the gas cell unit 55. The analyzing unit 50 of the present exemplary embodiment measures the optical absorbance in association with various flow rate values of the purge gas in order to estimate the influence of the purge gas and correct the above-described errors.

The measuring unit 76 calculates the light intensity ratio in association with at least two levels of the gas flow rate ratio. In the example shown in FIG. 7, the measuring unit 76 calculates the light intensity ratio at three levels r1, r2 and r3 of the flow rate ratio. The measuring unit 76 uses a plurality of calculated results to approximate the relation between the gas flow rate ratio and the light intensity ratio by a straight line 89. The gradient of the straight line 89 indicates how much the influence of the purge gas is. The light intensity ratio Po corresponding to the gas flow rate ratio of 0 on the straight line 89 denotes the light intensity ratio that is expected to be measured when the flow rate of the purge gas is set to 0.

The storage unit 88 may store thereon the above-described gradient of the straight line 89 as the second calibration information. The measuring unit 76 calculates the light intensity that is expected to be measured when the flow rate of the purge gas is set to 0, based on the light intensity ratio measured during normal operation, the gas flow rate ratio measured at the same timing and the gradient of the above-described straight line 89. For example, the measuring unit 76 calculates a straight line that goes through a measurement point corresponding to this light intensity ratio and this gas flow rate ratio and has the same gradient as the straight line 89. The measuring unit 76 then calculates the light intensity ratio corresponding to the gas flow rate ratio of 0 on the calculated straight line.

The measuring unit 76 detects the concentration of the substance under measurement corresponding to the calculated light intensity ratio, based on the first calibration information stored on the storage unit 88. In the above-described manner, the concentration of the substance under measurement contained in the to-be-analyzed gas can be detected without the influence of the optical absorption by the purge gas.

The measuring unit 76 may obtain the second calibration information for each level of the purge gas temperature. One of the levels r1, r2, r3, . . . of the flow rate ratio may be set to 0 when it is attempted to obtain the second calibration information. Stated differently, the measuring unit 76 may obtain the second calibration information using the measurements taken with the purge gas flow rate being set to 0.

Figure 8:
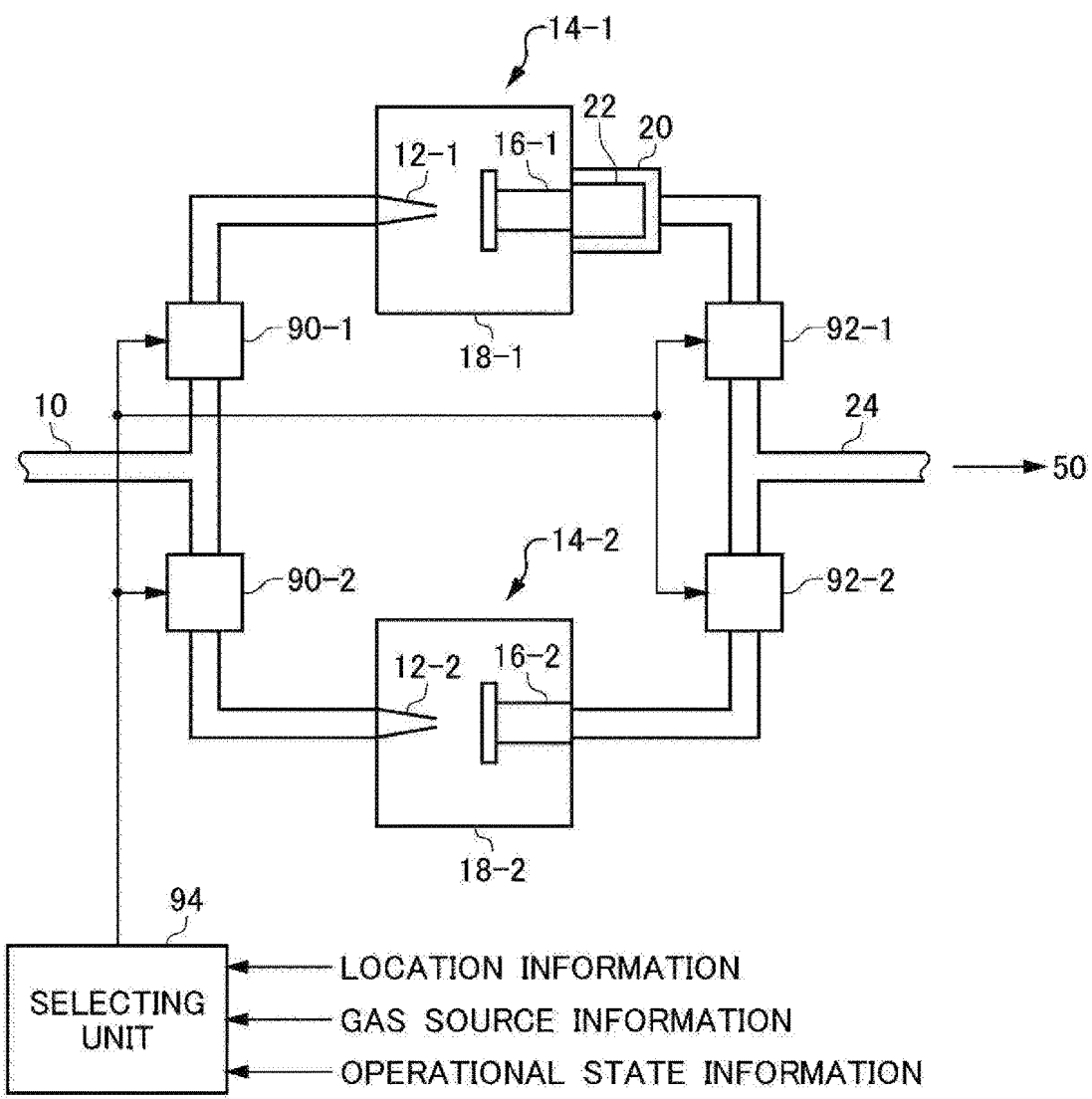
FIG. 8 shows an exemplary structure of the liquid collecting unit 14 and the dust collecting unit 20.

FIG. 8 shows an exemplary structure of the liquid collecting unit 14 and the dust collecting unit 20. The analyzing apparatus 100 of the present exemplary embodiment includes two liquid collecting units 14-1 and 14-2. The first liquid collecting unit 14-1 is connected to the dust collecting unit 20, and the second liquid collecting unit 14-2 is not connected to the dust collecting unit 20. Here, each of the liquid collecting units 14 is connected to the liquid discharging unit 30, but this is not shown in FIG. 8. A plurality of liquid discharging units 30 may be provided in a one-to-one correspondence with the liquid collecting units 14, or a portion of the discharge pipe 32 may be shared by the liquid collecting units 14.

The analyzing apparatus 100 of the present exemplary embodiment includes a selecting unit 94, a valve 90-1, a valve 90-2, a valve 92-1 and a valve 92-2. The collecting nozzle 10 has branches to be connected to the two liquid collecting units 14. The valves 90 are provided on the respective branches of the collecting nozzle 10. The connection tubes 24 extend respectively from the dust collecting unit 20 and the second liquid collecting unit 14-2 and merge before connected to the analyzing unit 50. The valves 92 are provided on the connection tubes 24 before they are merged.

The selecting unit 94 introduces the to-be-analyzed gas collected by the collecting nozzle 10 from the flue 210 into a selected one of the first liquid collecting unit 14-1 and the second liquid collecting unit 14-2. The first liquid collecting unit 14-1 can reduce the dust in the gas while the gas is passing therethrough when compared with the second liquid collecting unit 14-2 since the first liquid collecting unit 14-1 is connected to the dust collecting unit 20.

The selecting unit 94 may select the first liquid collecting unit 14-1 when the to-be-analyzed gas contains a considerable amount of dust, which is enough to contaminate the analyzing unit 50. The selecting unit 94 may select the second liquid collecting unit 14-2 when the to-be-analyzed gas contains some dust but the dust is not enough to contaminate the analyzing unit 50. For example, the selecting unit 94 selects the second liquid collecting unit 14-2 when the to-be-analyzed gas contains dust in such an amount that the purge gas flow can sufficiently protect the light emitting window 58 and the light receiving window 60. This feature can reduce the degradation of the filter 22 included in the dust collecting unit 20 and the filter 22 thus needs to be exchanged less frequently. Accordingly, when it is difficult to exchange the filter 22, for example, when the analyzing apparatus 100 is installed in a ship or the like, the filter 22 needs to be exchanged less frequently, which can reduce the workload.

The selecting unit 94 may select one of the first liquid collecting unit 14-1 and the second liquid collecting unit 14-2 based on the information provided by the gas source that has emitted the to-be-analyzed gas. For example, when the single flue 210 is configured to allow exhaust gases from a plurality of gas sources to pass therethrough, the selecting unit 94 may select one of the liquid collecting units 14 based on the information as to which one of the gas sources is in operation.

The selecting unit 94 may store therein in advance the information indicating how much dust is contained in the exhaust gas from each of the gas sources.

The selecting unit 94 may select one of the liquid collecting units 14 based on the information as to how much of the rated outputs are accounted for by the outputs generated by the gas sources emitting the exhaust gases. The selecting unit 94 may store therein in advance the information indicating the amount of dust in association with the output value of each of the gas sources.

The selecting unit 94 may select one of the liquid collecting units 14 based on the operational state of the scrubber apparatus that has treated the exhaust gas. Here, the operational state of the scrubber apparatus is indicated, for example, by one or both of the information indicating the amount of the exhaust gas introduced into the scrubber apparatus and the information indicating the amount of the sprayed mist of water. Generally speaking, as the ratio of the amount of the mist of water to the amount of the exhaust gas decreases, the dust contained in the exhaust gas that has passed through the scrubber apparatus relatively increases.

The selecting unit 94 may select one of the liquid collecting units 14 based on the location information of the analyzing apparatus 100. The location information of the analyzing apparatus 100 indicates, for example, the latitude, the longitude and the like. For example, when the analyzing apparatus 100 is used in a ship, different rules may apply to the exhaust gas depending on the location of the ship. The selecting unit 94 may select one of the liquid collecting units 14 based on the judgment as to whether the analyzing unit 50 needs to perform accurate analysis for a certain location.

For example, when the exhaust gas treating capability of the scrubber apparatus and the like is sufficiently higher than required by the exhaust-gas-related regulations imposed at the certain location, the selecting unit 94 may judge that highly accurate analysis is not necessary and select the second liquid collecting unit 14-2. In this case, the analysis performed by the analyzing unit 50 may provide more or less erroneous results due to the dust remaining in the to-be-analyzed gas. When the first liquid collecting unit 14-1 is selected, less dust remains in the to-be-analyzed gas. This makes it possible to measure the concentration of sulfur oxides and the like more accurately.

Figure 9:
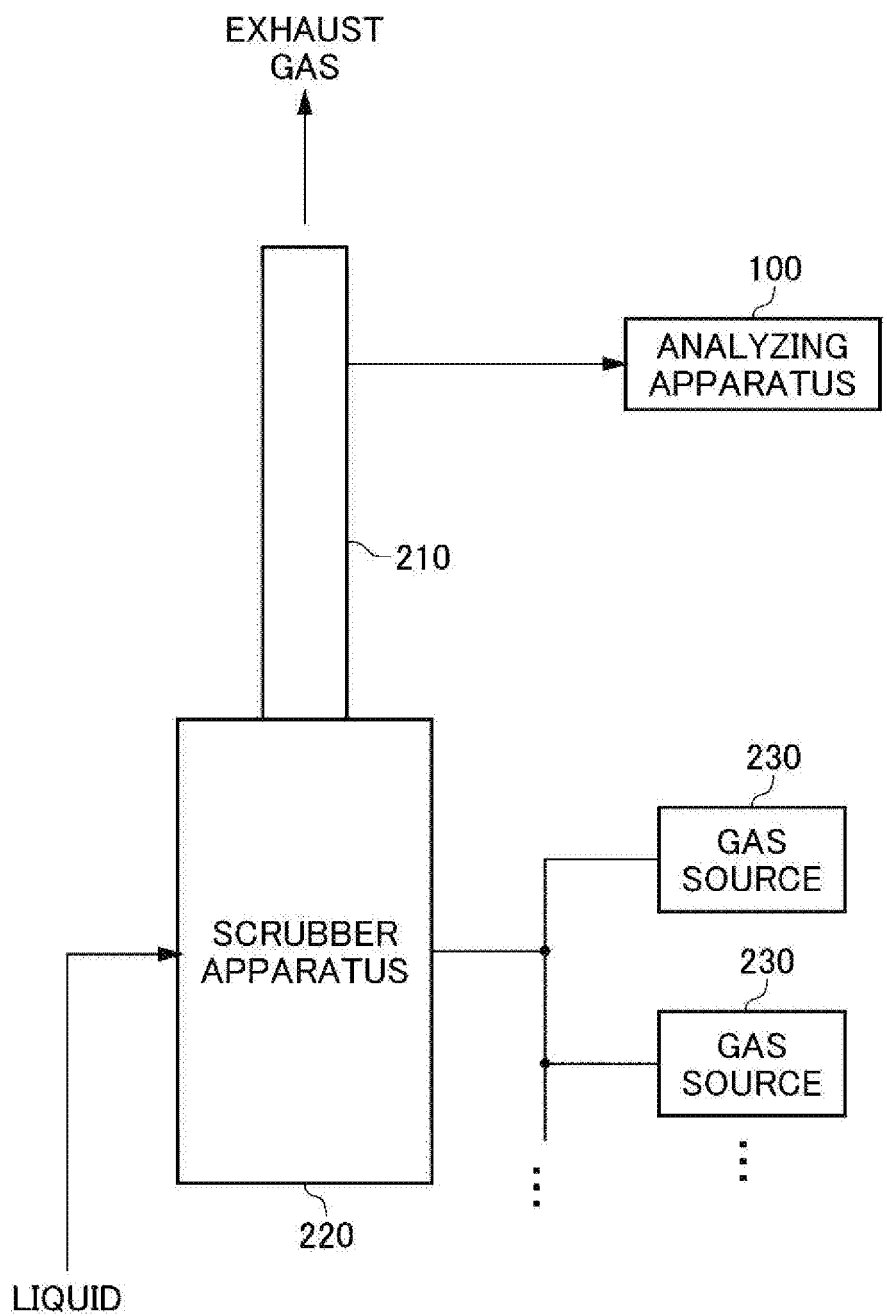
FIG. 9 shows an exemplary structure of an exhaust gas treating system 200 relating to an embodiment of the present invention.

FIG. 9 shows an exemplary structure of an exhaust gas treating system 200 relating to an embodiment of the present invention. The exhaust gas treating system 200 includes the analyzing apparatus 100, a scrubber apparatus 220 and the flue 210 and is configured to treat the exhaust gases emitted from one or more gas sources 230. The present exemplary embodiment is described with reference to a case where the exhaust gas treating system 200 is provided in a ship, but the exhaust gas treating system 200 can be used in different applications.

The respective gas sources 230 are main and auxiliary power sources for the ship engines, electric power sources for inboard facilities and the like, and generate mechanical, electrical and other power, as a result of which exhaust gases containing toxic substances such as sulfur oxides and the like are generated.

The scrubber apparatus 220 is configured to remove the toxic substances contained in the exhaust gases from the gas sources 230. The scrubber apparatus 220 may spray liquids to the exhaust gases to allow the liquids to absorb the toxic substances. When the exhaust gas treating system 200 is used for a ship, the liquids may be the seawater around the ship, water prepared in advance or the like. The exhaust gas treating system 200 may treat the liquids that have been used in the scrubber apparatus 220 with the use of chemical agents and the like to allow the liquids to be reusable in the scrubber apparatus 220.

The exhaust gas treating system 200 may further include a dust removing apparatus configured to remove the dust contained in the exhaust gases before the exhaust gases are introduced into the scrubber apparatus 220. The exhaust gas treating system 200 may further include a thermoelectric conversion apparatus configured to convert the heat of the exhaust gases into electricity before the exhaust gases are introduced into the scrubber apparatus 220.

The analyzing apparatus 100 is the same as the analyzing apparatus 100 described with reference to FIGS. 1 to 8. The analyzing apparatus 100 collects part of the exhaust gas passing through the flue 210 connected to the scrubber apparatus 220 to analyze the concentration of the toxic substances contained in the exhaust gas. The analyzing apparatus 100 of the present exemplary embodiment collects part of the exhaust gas. The analyzing apparatus 100 of the present exemplary embodiment then measures the optical absorption spectrum of the exhaust gas in the analyzing unit 50, which is independent of the flue 210, to analyze the gas components of the exhaust gas.

A technique is possible to provide a light receiving unit and a light emitting unit on the side wall of the flue 210 to measure an optical absorption spectrum. In this case, the distance between the light receiving unit and the light emitting unit is dependent on the diameter of the flue 210. For this reason, the distance between the light receiving unit and the light emitting unit cannot be appropriately determined, and it may be difficult to achieve an appropriate optical path length for the light traveling through the gas.

Having the gas cell unit 55, which is independent from the flue 210, the analyzing apparatus 100 of the present exemplary embodiment can provide an appropriate distance between the light receiving unit and the light emitting unit. For this reason, the analyzing apparatus 100 of the present exemplary embodiment can accurately analyze the gas components. In addition, when the concentration of the toxic substances contained in the exhaust gas goes beyond an allowable range, the analyzing apparatus 100 may issue a warning to a user or control the scrubber apparatus 220 and the gas sources 230 and the like to lower the concentration of the toxic substances.

The analyzing apparatus 100 can analyze the gas components of the exhaust gas after removing at least part of the liquid components contained in the exhaust gas. Accordingly, the analyzing apparatus 100 can reduce the influence of the optical absorption of the liquids and accurately analyze the gas components. In addition, the analyzing apparatus 100 can sequentially discharge the collected liquid components. Thus, the analyzing apparatus 100 can prevent the collected liquid components from changing the concentration of the substance under measurement contained in the to-be-analyzed gas and can be smaller.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF THE REFERENCE NUMERALS

10 . . . collecting nozzle, 12 . . . injection opening, 13 . . . plate-like portion, 14 . . . liquid collecting unit, 15 . . . separating plate, 16 . . . separating and collecting unit, 17 . . . gas flow hole, 18 . . . collecting case, 20 . . . dust collecting unit, 22 . . . filter, 24 . . . connection tube, 26 . . . gas discharging unit, 30 . . . liquid discharging unit, 32 . . . discharge pipe, 34 . . . first region, 36 . . . second region, 38 . . . third region, 40 . . . fourth region, 42 . . . funnel, 50 . . . analyzing unit, 52 . . . spectroscopic measuring unit, 54 . . . light emitting unit, 55 . . . gas cell unit, 56 . . . light receiving unit, 58 . . . light emitting window, 60 . . . light receiving window, 62 . . . purge gas inlet, 64 . . . purge tube, 65 . . . purge unit, 66 . . . purge pump, 68 . . . gas outlet, 70 . . . gas discharge pump], 72 . . . to-be-analyzed gas inlet, 74 . . . gas introducing pump, 76 . . . measuring unit, 78 . . . flow rate control unit, 80 . . . region, 82 . . . optical path, 83 . . . extension unit, 84 . . . calibration gas inlet, 85 . . . calibration gas outlet, 86 . . . calibration gas introducing unit, 88 . . . storage unit, 89 . . . straight line, 90 . . . valve, 92 . . . valve, 94 . . . selecting unit, 100 . . . analyzing apparatus, 200 . . . exhaust gas treating system, 210 . . . flue, 212 . . . flange, 220 . . . scrubber apparatus, 230 . . . gas source

The invention claimed is:

1. An analyzing apparatus for analyzing a gas component, comprising:
a collecting nozzle configured to collect a to-be-analyzed gas passing through a flue;
a liquid collecting unit configured to collect a liquid component contained in the to-be-analyzed gas collected by the collecting nozzle and to allow the to-be-analyzed gas to pass therethrough;
a liquid discharging unit configured to discharge the liquid component collected by the liquid collecting unit; and
an analyzing unit configured to analyze a gas component of the to-be-analyzed gas that has passed through the liquid collecting unit, wherein
the collecting nozzle has an injection opening configured to inject the to-be-analyzed gas toward the liquid collecting unit,
the liquid collecting unit includes:
a separating and collecting unit configured to separate the liquid component contained in the to-be-analyzed gas and to allow the to-be-analyzed gas to pass therethrough; and
a collecting case enclosing therein the separating and collecting unit and the injection opening of the collecting nozzle,
the liquid discharging unit includes a discharge pipe configured to discharge the liquid component into the flue,
the discharge pipe is provided with a tapered funnel at an end opposing an opening provided at a bottom of the collecting case, the tapered funnel having a first opening facing the bottom of the collecting case and a second opening facing away from the collecting case and having a diameter smaller than a diameter of the first opening,
the discharge pipe includes:
a first region having a portion extending downwards from the bottom of the collecting case;
a second region connected to an end of the first region and having a straight portion extending in a direction parallel to the bottom of the collecting case or an arch-like portion;
a third region having a portion extending upwards from an end of the second region; and
a fourth region having a portion extending horizontally from an end of the third region and positioned lower than the bottom of the collecting case, the fourth region being inserted into the flue.

2. The analyzing apparatus as set forth in claim 1, wherein the first region or the fourth region is configured to prevent the discharged liquid from flowing back into the collecting case.

3. The analyzing apparatus as set forth in claim 1, wherein a portion of the first, second, and third regions form a reservoir unit configured to store therein the liquid component between the collecting case and the flue so that the stored liquid component seals the discharge pipe.

4. The analyzing apparatus as set forth in claim 1, wherein the analyzing unit includes:
a light emitting unit having therein a light emitting window through which light passes;
a light receiving unit having therein a light receiving window through which light passes;
a gas cell unit arranged between the light emitting unit and the light receiving unit and configured to allow the to-be-analyzed gas to be introduced thereinto after passing through the liquid collecting unit; and a purge unit configured to introduce a purge gas into at least one of a region in the gas cell unit that opposes the light emitting window and a region in the gas cell unit that opposes the light receiving window.

5. The analyzing apparatus as set forth in claim 4, wherein the analyzing unit further includes a measuring unit configured to analyze the gas component of the to-be-analyzed gas based on an optical path length determined by a distance between the light emitting window and the light receiving window and a predetermined optical path length correction value.

6. The analyzing apparatus as set forth in claim 4, wherein the analyzing unit further includes a flow rate control unit configured to control a flow rate of the purge gas to be introduced into the gas cell unit based on a flow rate of the to-be-analyzed gas introduced from the liquid collecting unit to the gas cell unit.

7. The analyzing apparatus as set forth in claim 6, wherein the analyzing unit further includes:

a calibration gas introducing unit configured to introduce a calibration gas into the gas cell unit;

a measuring unit configured to measure intensity of light received by the light receiving unit for each value of a flow rate ratio between the calibration gas and the purge gas; and a storage unit configured to store therein calibration information based on the intensity of the light measured by the measuring unit in association with each value of the flow rate ratio.

8. The analyzing apparatus as set forth in claim 7, wherein the measuring unit analyzes the gas component of the to-be-analyzed gas based on (i) intensity of light received by the light receiving unit when the to-be-analyzed gas and the purge gas are introduced into the gas cell unit and (ii) the calibration information stored in the storage unit.

9. The analyzing apparatus as set forth in claim 4, wherein the light emitting unit emits light having a wavelength in an infrared or ultraviolet region.

10. The analyzing apparatus as set forth in claim 4, wherein the gas cell unit has a plurality of inlets to introduce the to-be-analyzed gas thereinto, and the plurality of inlets are arranged in a nonparallel manner to an axis extending from the light emitting unit to the light receiving unit.

11. The analyzing apparatus as set forth in claim 10, wherein the plurality of inlets are arranged at equal intervals in a side wall of the gas cell unit.

12. The analyzing apparatus as set forth in claim 1, wherein the analyzing apparatus comprises two liquid collecting units, a first liquid collecting unit of the two liquid collecting units is connected to a dust collecting unit configured to collect dust contained in the to-be-analyzed gas, a second liquid collecting unit of the two liquid collecting units is not connected to the dust collecting unit, and the analyzing apparatus further includes a selecting unit configured to introduce the to-be-analyzed gas collected by the collecting nozzle into a selected one of the first liquid collecting unit and the second liquid collecting unit.

13. The analyzing apparatus as set forth in claim 12, wherein the selecting unit selects one of the first liquid collecting unit and the second liquid collecting unit based on location information of the analyzing apparatus.

14. The analyzing apparatus as set forth in claim 12, wherein the selecting unit selects one of the first liquid collecting unit and the second liquid collecting unit based on information regarding a gas source that has emitted the to-be-analyzed gas.

15. The analyzing apparatus as set forth in claim 12, wherein the to-be-analyzed gas has passed through a scrubber apparatus, and the selecting unit selects one of the first liquid collecting unit and the second liquid collecting unit based on an operational state of the scrubber apparatus.

16. The analyzing apparatus as set forth in claim 1, wherein the to-be-analyzed gas has passed through a scrubber apparatus.

17. An exhaust gas treating system comprising:

the analyzing apparatus as set forth in claim 16; and the scrubber apparatus.

* * * * *